(12) United States Patent
Rehe

(10) Patent No.: US 9,215,965 B2
(45) Date of Patent: Dec. 22, 2015

(54) ENDOSCOPE

(75) Inventor: Oliver Rehe, Tuttlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 198 days.

(21) Appl. No.: 13/439,061

(22) Filed: Apr. 4, 2012

(65) Prior Publication Data

US 2012/0265018 A1    Oct. 18, 2012

(30) Foreign Application Priority Data

Apr. 12, 2011    (DE) .......................... 10 2011 007 190

(51) Int. Cl.
*A61B 1/00* (2006.01)
*A61B 1/04* (2006.01)
*A61B 1/06* (2006.01)
*G02B 23/24* (2006.01)

(52) U.S. Cl.
CPC ......... *A61B 1/00096* (2013.01); *A61B 1/00183* (2013.01); *A61B 1/04* (2013.01); *G02B 23/2423* (2013.01)

(58) Field of Classification Search
CPC ........... A61B 1/00096; A61B 1/00163; A61B 1/00174; A61B 1/00177; A61B 1/00179; A61B 1/00181; A61B 1/00183; A61B 1/00172; A61B 1/005; A61B 1/0051
USPC ......... 600/107, 109–113, 127–130, 157, 160, 600/166–181
See application file for complete search history.

(56) References Cited

U.S. PATENT DOCUMENTS

| | | | |
|---|---|---|---|
| 3,809,072 A | 5/1974 | Ersek et al. | |
| 3,856,000 A | 12/1974 | Chikama | |
| 4,140,364 A | 2/1979 | Yamashita et al. | |
| 5,693,043 A | 12/1997 | Kittrell et al. | |
| 6,413,209 B1 | 7/2002 | Thompson | |
| 2003/0092966 A1 | 5/2003 | Schara et al. | |
| 2003/0171652 A1* | 9/2003 | Yokoi et al. | 600/160 |
| 2004/0236183 A1* | 11/2004 | Durell | 600/173 |
| 2005/0043587 A1* | 2/2005 | Fujimori et al. | 600/160 |
| 2006/0256450 A1* | 11/2006 | Tesar et al. | 359/727 |
| 2007/0002135 A1* | 1/2007 | Glukhovsky | 348/77 |
| 2007/0118018 A1* | 5/2007 | Gilad et al. | 600/160 |
| 2008/0208006 A1 | 8/2008 | Farr | |
| 2009/0177094 A1 | 7/2009 | Brown et al. | |
| 2009/0306474 A1 | 12/2009 | Wilson | |
| 2010/0030031 A1* | 2/2010 | Goldfarb et al. | 600/163 |
| 2010/0324372 A1 | 12/2010 | Buerk et al. | |
| 2011/0028790 A1 | 2/2011 | Farr et al. | |
| 2012/0136213 A1 | 5/2012 | Weimer et al. | |
| 2012/0232408 A1 | 9/2012 | Weller-Brophy | |

FOREIGN PATENT DOCUMENTS

| | | | |
|---|---|---|---|
| DE | 102009025660 | 12/2010 | |
| JP | 2004154300 A | * 6/2004 | .............. A61B 1/00 |

* cited by examiner

*Primary Examiner* — Ryan Henderson
(74) *Attorney, Agent, or Firm* — Skaar Ulbrich Macari, P.A.

(57) ABSTRACT

An endoscope is provided, with a first tube, a cover glass arranged at the distal end of the first tube, as well as with imaging optics, arranged in the first tube, which image an object located in front of the cover glass as an image, wherein the cover glass has a spherically curved, concave inside, a spherically curved, convex outside, and a constant thickness.

16 Claims, 3 Drawing Sheets

ENDOSCOPE

PRIORITY

The present application claims priority to German Application No. 102011007190.3, filed Apr. 12, 2011, which is hereby incorporated by reference in its entirety.

FIELD

The present invention relates to an endoscope with a first tube, a cover glass arranged at the distal end of the first tube, as well as imaging optics, arranged in the first tube, which image an object located in front of the cover glass as an image.

BACKGROUND

The cover glass is often formed as a coplanar sheet. As, to image the object by means of the imaging optics, light beams pass from the object through the cover glass, the difficulty arises that these light beams are refracted to different degrees depending on the medium (e.g. air, liquid, etc.) present on the outside of the cover glass. Naturally, this affects the imaging quality.

If the endoscope is formed as an endoscope with variable viewing direction, the refraction of the light beams additionally depends on the viewing direction.

SUMMARY

It is an object of certain embodiments of the invention to provide an endoscope with improved imaging that addresses the issues discussed above. The object is achieved in the case of an endoscope in that the cover glass including a spherically curved, concave inside, a spherically curved, convex outside, and a constant thickness. The light beams coming from every object point and used for the image generation thereby advantageously pass through the cover glass perpendicularly or substantially perpendicularly with the result that the cover glass brings about no or only a very small refraction. As a result, the influence of the medium on the outside of the cover glass in the case of the endoscope according to the invention is very greatly reduced compared with a known endoscope.

In the case of the endoscope according to certain embodiments of the invention, the cover glass can extend, in a first plane, over a first angle range and, in a second plane which is perpendicular to the first plane, over a second angle range, wherein the first angle range is larger than the second angle range. In particular, the first angle range can be at least 1.5 times or at least 2 times as large as the second angle range. This is advantageous in particular in the case of an endoscope with variable viewing direction, wherein the first angle range is preferably chosen such that all possible viewing directions are covered.

In the case of the endoscope according to certain embodiments of the invention, the inside can be antireflection-coated. Furthermore, in addition or alternatively, the outside can be antireflection-coated. This improves the imaging properties.

Furthermore, the edge of the cover glass can be soldered to the distal end of the first tube. The distal end of the first tube can thus be formed hermetically sealed. In particular, the endoscope can thereby be autoclavable. Naturally, any other type of connection between the cover glass and the distal end of the first tube is also possible. Thus, e.g. the cover glass can be adhesively secured to the distal end of the first tube.

The cover glass can be formed from plastic or glass. It is preferably formed from sapphire glass.

In the case of the endoscope according to certain embodiments of the invention, the imaging optics can have a swivellably housed deflecting element with which the viewing direction through the cover glass can be set. The deflecting element can be in particular a deflecting prism or a mirror. The rotational axis of the deflecting element is preferably perpendicular to the longitudinal direction of the first tube.

Furthermore, the deflecting element can be secured in a rotatably housed holder and can be rotated about its rotational axis by means of a draw tube which is positioned together with the first tube in an endoscope shaft of the endoscope. For this, for example, the proximal end of the draw tube can be moved axially via an actuating element arranged on a handle of the endoscope. In particular, the actuating element can be mechanically connected to the draw tube via a gear mechanism. The gear mechanism can preferably be formed such that it converts a rotational movement of the actuating element into an axial movement of the draw tube.

Preferably, a further illumination channel via which the object to be imaged can be illuminated is provided in or on the first tube. Illumination can take place for example by means of optical fibres which can be impacted by light at the handle of the endoscope. Naturally, other types of illumination are also possible. In particular, a light source (e.g. one or more LED diodes) can be provided for illumination at the distal end of the first endoscope shaft.

In the case of the endoscope according to certain embodiments of the invention, the centres of the radii of curvature of the inside and the outside can coincide and lie on or close to the swivel axis of the deflecting element and/or in or close to a surface of the deflecting element bringing about the beam deflection. Excellent optical imaging properties can thus be achieved.

In the case of the endoscope according to certain embodiments of the invention, the cover glass can have a flat lateral face, connecting the inside and the outside, which is inclined relative to the radii of curvature of the inside and the outside. In particular, the lateral face can have a left and a right section which are parallel to each other. Furthermore, the lateral face can have two opposite end faces which are each formed rounded seen in top view. Furthermore, the vertex lines of the rounded end faces can be tilted towards each other by 90°. The formation of such a lateral face makes the production and testing of the produced cover glass easier.

In the case of the endoscope according to certain embodiments of the invention, the imaging optics can have several lenses, wherein the lens of the imaging optics positioned closest to the cover glass is formed as a flat-concave lens the flat side of which faces the cover glass or as a concave-concave lens, wherein the side facing the cover glass is then, naturally, curved concavely.

As the flat or the concave side faces the cover glass, a negative lens with high refractive power is advantageously positioned close to the cover glass, whereby the radial extent of the imaging optics can be reduced while imaging properties remain the same or almost the same.

The endoscope according to certain embodiments of the invention can be formed in particular as a rigid endoscope (thus as an endoscope with a rigid endoscope shaft). However, it is also possible that the endoscope shaft can be bent out at least in one section.

Furthermore, the endoscope can have an eyepiece on the handle, and/or an interface for e.g. a video camera. Alternatively, it is possible that the endoscope contains at the distal end an image sensor arranged downstream of the imaging optics.

The endoscope can have further elements known to a person skilled in the art which are necessary for operating the endoscope.

It is understood that the features mentioned above and those yet to be explained below can be used, not only in the stated combinations, but also in other combinations or alone, without departing from the scope of the present invention.

BRIEF DESCRIPTION OF THE DRAWINGS

The invention is explained in further detail below by way of example using the attached drawings which also disclose features essential to the invention. There are shown in.

DETAILED DESCRIPTION

In the following descriptions, the present invention will be explained with reference to example embodiments thereof. However, these example embodiments are not intended to limit the present invention to any specific example, environment, embodiment, applications or particular implementations described in these example embodiments. Therefore, descriptions of these example embodiments are only for purposes of illustration rather than limitation to the invention. It should be appreciated that in the following example embodiments and the attached drawings, elements unrelated to the present invention are omitted from depiction; and dimensional relationships among individual elements in the attached drawings are illustrated only for ease of understanding, but not to limit the actual scale.

Figure 1:
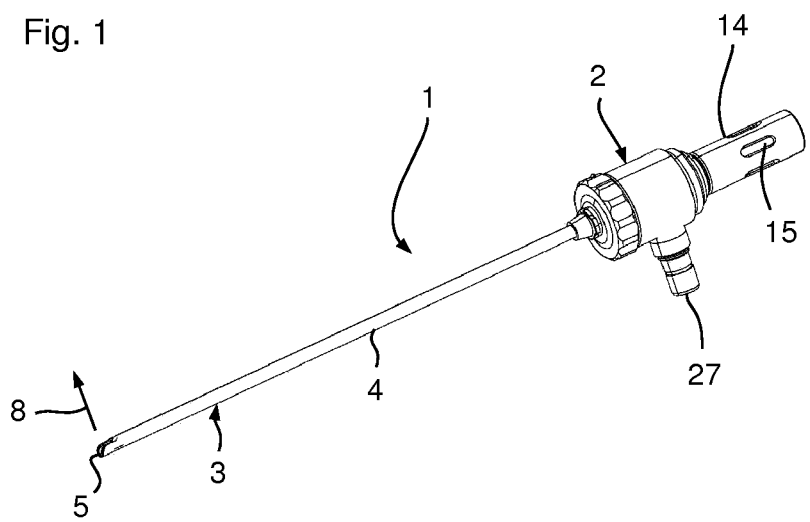
FIG. 1 is a perspective view of an embodiment of the endoscope according to the invention.

In the embodiment shown in FIG. 1, the endoscope 1 according to the invention is formed as an endoscope 1 with variable viewing direction and has a handle 2 as well as an endoscope shaft 3, the casing tube 4 of which can be seen in FIG. 1, connected to the handle 2.

Figure 2:
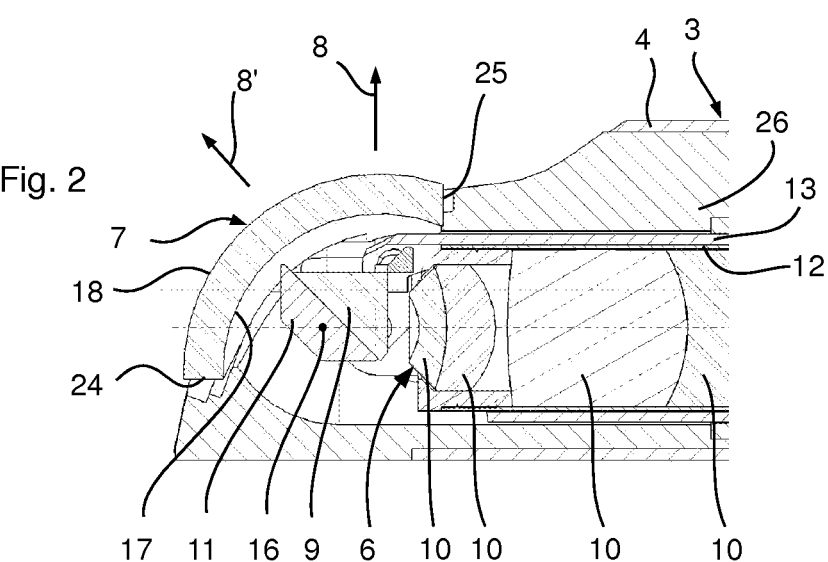
FIG. 2 is an enlarged sectional view of the distal end of the endoscope shaft 3.

As can be seen in particular from the enlarged sectional representation of the distal end 5 of the endoscope shaft 3 in FIG. 2, imaging optics 6 are arranged in the endoscope shaft 3 and a cover glass 7 is positioned at the distal end 5. An object located in front of the cover glass 7 in viewing direction 8 of the imaging optics 6 can be imaged as an image with the imaging optics 6.

The imaging optics 6 comprise a deflecting prism 9 as well as lenses 10 arranged downstream of this. The deflecting prism 9 sits in a prism holder 11 which is swivellably housed at the distal end of an optics tube 12 arranged in the endoscope shaft 3.

The optics tube 12 is positioned in a draw tube 13 and the draw tube 13 is housed displaceable relative to the optics tube 12 and to the casing tube 4 in longitudinal direction of the endoscope shaft 3, wherein the axial position of the draw tube 13 can be set by means of an actuating element 14 arranged on the handle 2. The actuating element 14 is here formed as a sleeve which is housed rotatable about the longitudinal axis of the endoscope shaft 3 and has recesses 15 for better manipulability. A rotation of the actuating element 14 via a coupling mechanism, not shown, results in an axial displacement of the draw tube 13. The distal end of the draw tube 13 is coupled to the prism holder 11 such that an axial displacement of the draw tube results in a rotation of the prism holder 11 and thus of the deflecting prism 9 about the rotational axis 16 shown schematically in FIG. 2. This rotation of the deflecting prism 9 results in an alteration of the viewing direction 8, for example to the viewing direction 8' drawn in schematically in FIG. 2.

The imaging optics 6 here also have an image-transmission system in the form of rod lenses, not shown, in the endoscope shaft 3 which serves to transmit the recorded image to the proximal end of the handle 2, where it is then made available. The image made available can be observed directly or via a proximally arranged eyepiece (for example inside the handle 2). It is also possible to attach a video camera to the proximal end of the handle 2, which records the image and can display it via an output device (for example a monitor).

The cover glass 7 has a spherically curved, concave inside 17 and a spherically curved, convex outside 18, wherein the centres of curvature of inside and outside 17, 18 coincide (drawn in as point M in FIGS. 5, 8 and 9), with the result that the thickness of the cover glass 7 is constant. By thickness is meant here in particular the distance between inside and outside in radial direction (thus starting from the centres of curvature). The cover glass 7 can therefore also be called a domed glass.

This formation of the cover glass 7 results in the great advantage that the beams coming from every object point and used for the image generation pass through the cover glass 7 perpendicularly or substantially perpendicularly. The cover glass 7 can therefore be regarded as an element that is substantially neutral for the imaging (which has essentially no optical imaging properties), with the result that, when the beams pass through the cover glass 7, no or essentially negligible refraction occurs, regardless of the medium present on the outside 18 of the cover glass 7, as well as regardless of the viewing direction 8, 8' set by the swivel position of the deflecting prism 9. This advantage can be exploited particularly well when the centres of curvature of the inside and the outside 17, 18 lie on or close to the swivel axis 16, wherein the swivel axis 16 lies preferably in the side of the deflecting prism 9 which brings about the beam deflection. Naturally, it is also possible to deviate to a greater or lesser extent from these optimum conditions for optical imaging if this is necessary e.g. because of the space there for the imaging optics 6 and in particular for the deflection of the deflecting prism 9.

Although, because of the opening angle, used for the imaging, of the beams coming from every object point, a refraction cannot be prevented for all beams, it is much smaller compared with other shapes of cover glass, such as e.g. when the cover glass is formed as a coplanar sheet. If a coplanar sheet were to be used as cover glass, the refraction would depend very greatly on the surrounding medium (e.g. air or a liquid)

on the one hand and also greatly on the just chosen viewing direction 8, 8' on the other hand.

Figure 3:
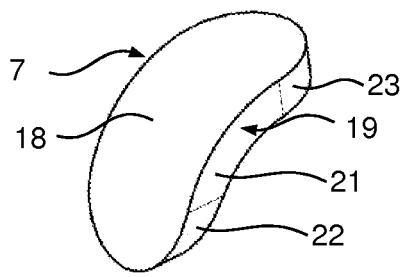
FIG. 3 is a first perspective view of the cover glass 7.
Figure 4:
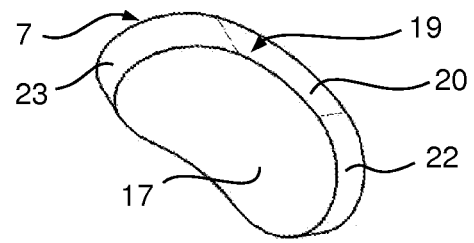
FIG. 4 is a second perspective view of the cover glass 7.

Perspective views of the cover glass 7 are represented in FIGS. 3 and 4. It can be seen from these representations that the cover glass 7, seen in top view, is no longer round, as has been usual until now, but rather has an oblong shape with rounded narrow sides.

Figure 5:
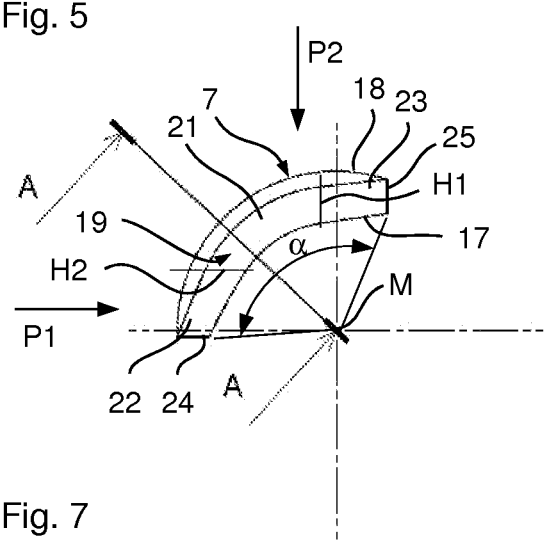
FIG. 5 is a side view of the cover glass 7.
Figure 6:
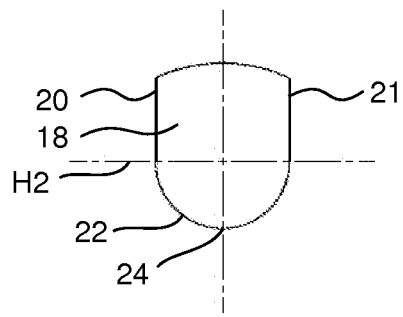
FIG. 6 is a view of the cover glass in the direction of the arrow P1 in FIG. 5.
Figure 7:
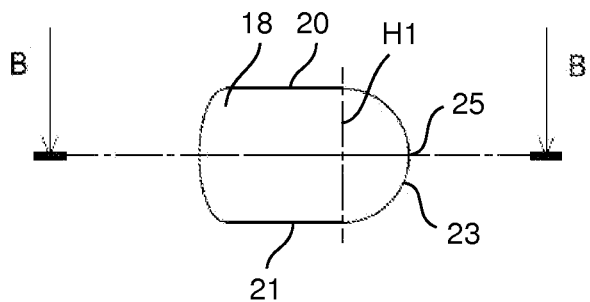
FIG. 7 is a view of the cover glass in the direction of the arrow P2 in FIG. 5.
Figure 8:
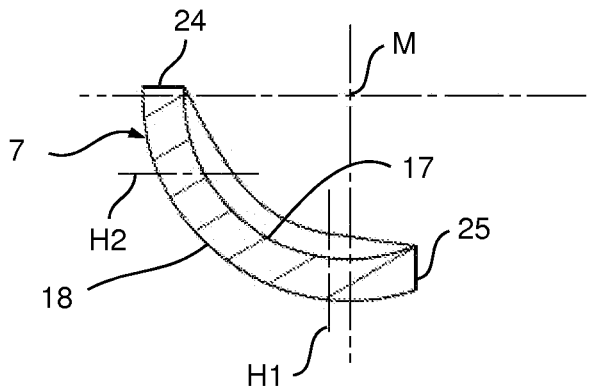
FIG. 8 is an enlarged sectional representation of the cover glass along the section line A-A from FIG. 5.
Figure 9:
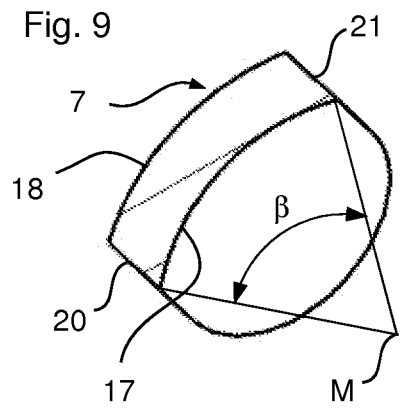
FIG. 9 is an enlarged sectional representation of the cover glass along the section line B-B from FIG. 7.

The cover glass is represented in side view in FIG. 5, the view shown in FIG. 6 is in the direction of the arrow P1 and the view shown in FIG. 7 is in the direction of the arrow P2. FIG. 8 shows the enlarged sectional representation A-A according to FIG. 5, and FIG. 9 shows the enlarged sectional representation B-B according to FIG. 7.

As can be seen from the representation in FIG. 5, the cover glass 7 extends over the angle range α in a first plane and, in a second plane perpendicular thereto, the cover glass 7 extends over the angle range β (FIG. 9), wherein the first angle range α is larger than the second angle range β. Because of these different angle ranges α, β, the described oblong shape of the cover glass 7 results. In the embodiment described here, the first angle range α is almost twice as large as the second angle range β.

The inside and the outside 17 and 18 are connected to an edge 19 which is formed as a flat lateral face. The alignment of the lateral face 19, however, is not radial starting from the centres of curvature of the inside and the outside 17, 18, but inclined towards this radial direction.

Thus, the lateral face 19 has a left and a right section 20, 21 on the long sides of the cover glass 7 which extend parallel to each other. The left and right sections 20, 21 are connected to each other via a lower end section 22 and an upper end section 23, wherein in the region of the two end sections 22 and 23 the outside 18, seen in top view, is rounded, as can be seen in particular in FIGS. 6 and 7. Naturally, the same applies, in a view seen from below, to the inside 17. The two end sections 22 and 23 are each formed such that their crown lines (lower crown line 24 in the case of the lower end section 22 and upper crown line 25 in the case of the upper end section 23) are tilted towards each other by 90°. The lateral face 19 can thus also be called a straight lateral face. This formation of the lateral face 19 makes it easier to produce the cover glass 7 as well as also to connect the cover glass 7 to an inner tube 26 of the endoscope 1 in the manner described below. The transition point between the left and right sections 20, 21 with the respective end sections 22 and 23 is represented by auxiliary lines H1 and H2 in FIGS. 5-8.

The inside 17 of the cover glass 7, which is formed here as a sapphire cover glass, is provided with a non-reflective coating and is thus non-reflective. Naturally, in addition or alternatively, the outside 18 can be non-reflective.

The cover glass 7 is here soldered by its edge 19 to the distal end of the inner tube 26 such that the opening at the distal end of the inner tube 26 is hermetically sealed (FIG. 2). The draw tube 13 sits inside the inner tube 26, and the inner tube 26 is, for its part, surrounded by the casing tube 4, wherein there is in customary manner at least one space, extending in the axial direction of the casing tube 4 between the inner tube 26 and the casing tube 4, in which optical fibres (not shown) are arranged which serve to illuminate the object to be imaged. The optical fibres can be impacted by light via an optical-fibre connection 27 on the handle 2.

In order to make it easier to solder the cover glass 7 to the inner tube 26, the edge 19 can be provided with a solderable metal layer.

Naturally, it is also possible for the cover glass 7 to be adhesively secured to the distal end of the inner tube 26 or connected in another way.

Figure 10:
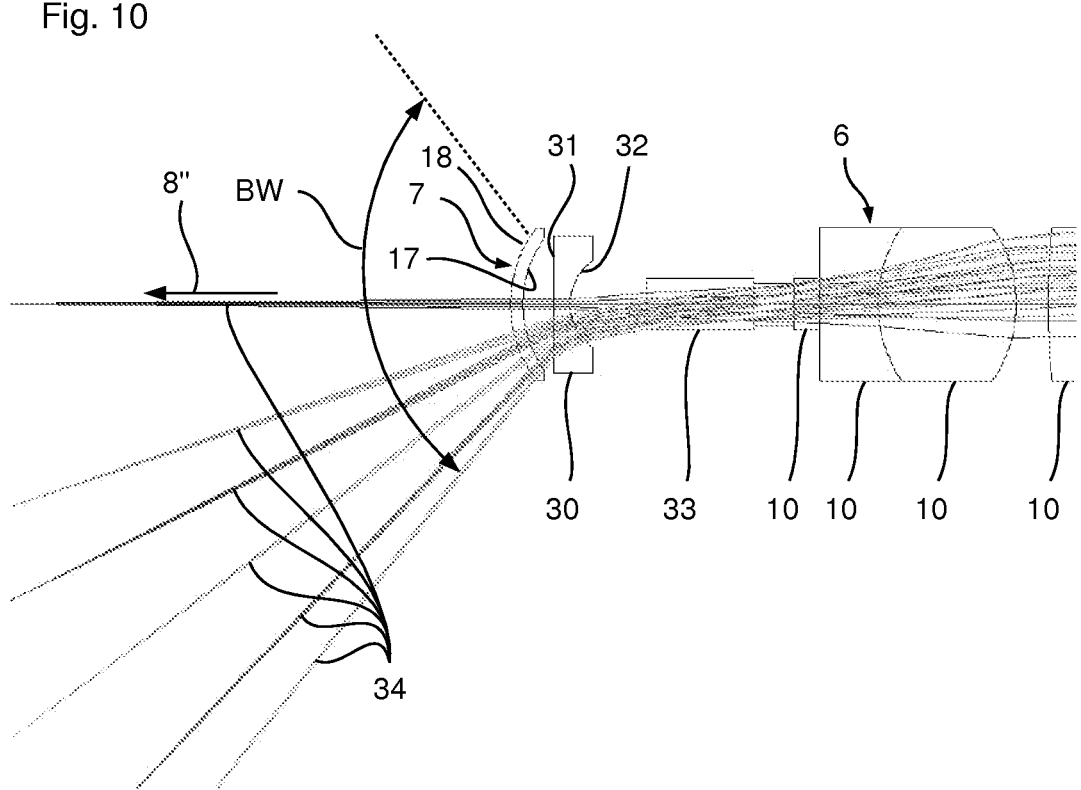
FIG. 10 is a schematic sectional view of cover glass and imaging optics of an endoscope according to the invention according to a further embodiment.

The cover glass 7 and the imaging optics 6 of a further embodiment of the endoscope 1 according to the invention are shown in FIG. 10 in schematic sectional view.

Unlike the embodiment described in connection with FIGS. 1 to 9, the imaging optics 6 in the variant according to FIG. 10 have a flat-convex lens 30 which is formed as a negative lens and, of all the lenses 30, 10 of the imaging optics 6, is positioned closest to the cover glass 7, wherein the flat side 31 of the lens 30 faces towards the cover glass 7 and the concave side 32 of the lens 30 faces away from the cover glass 7.

Furthermore, a few light bundles 34 which indicate half of the image angle BW which can be recorded with the endoscope 1 are also represented in FIG. 10 by way of example.

In the embodiment according to FIG. 10, the inside and the outside 17, 18 are again spherically curved, wherein their centres of curvature coincide. In particular, the endoscope is formed such that the two centres of curvature coincide with the entrance pupil of the imaging optics 6. The position of the entrance pupil is determined by the intersection point of all the main beams (or central light beam of the represented light bundles 34) and is ideally one point. Due to the presence of pupil aberrations in the actual imaging optics 6, the entrance pupil is most often slightly curved and cannot be found precisely in one point. In this case, a compromise is sought regarding the position of the centres of curvature of the inside and the outside 17, 18 of the cover glass 7. For example, the centres of curvature can lie in the centre of the different intersection points of the main beams. The curvature of the outside 18 of the cover glass 7 is chosen in particular such that the main beams of all light bundles from the image angle BW strike the outside 18 at right angles.

The wall thickness of the cover glass 7 can be e.g. in the range of from 0.1 to 0.3 mm. In the embodiment described here, the wall thickness is for example 0.2 mm.

With such a cover glass, which can also be called a null lens, it is possible that the image angle of the endoscope does not change or changes only barely if the cover glass is in air or e.g. in a saline solution or another transparent medium, in particular a transparent liquid medium. Because of the flat side 31, the distal lens 30 has a higher refraction compared with a distal lens in which the side facing the cover glass 7 is formed convexly curved, whereby the imaging optics 6 can be formed overall with a smaller diameter for the same image angle BW.

The cover glass 7 is formed in particular from glass or crystal. For example the cover glass can be formed as a sapphire cover glass. In particular, the cover glass is formed from a chemically inert material which has e.g. a predetermined hardness.

In the representation shown in FIG. 10, it was initially assumed that there is a viewing direction 8" of 0°. The viewing direction 8" in this case runs parallel to the longitudinal axis of the endoscope shaft 3 (FIG. 1) or parallel to the optical axis of the imaging optics 6. For endoscopes which have viewing directions other than one of 0°, the optical structure according to FIG. 10 can be used in the same way. In this case, the deflecting element (for example prism) drawn in schematically with the reference number 33 is provided.

In a variant, the distal lens can be formed as a concave-concave lens, wherein such a formation again advantageously results in a distal lens whose side facing the cover glass is concavely curved.

Naturally, in the embodiment described in connection with FIGS. 1 to 9, the distal lens 10 of the imaging optics 6 (thus the lens 10 which is positioned closest to the cover glass 7) can also be formed as a flat-concave lens 30, wherein the flat side 31 faces the cover glass 7, or as a concave-concave lens 30. The distal lens 30 can in this case either be positioned between the deflecting prism 9 and the cover glass 7 or be arranged downstream of the deflecting prism 9, with the result that in this case the light beams first pass through the cover glass 7, are deflected by means of the deflecting prism 9 and then strike the distal lens 30.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An endoscope, comprising:
   a first tube; and
   a cover glass arranged at a distal end of the first tube, as well as with imaging optics, arranged in the first tube, which image an object located in front of the cover glass as an image,
   wherein the cover glass has a spherically curved, concave interior surface having the same radius of curvature along an entirety of the interior surface, a spherically curved, convex exterior surface having the same radius of curvature along an entirety of the exterior surface, a constant thickness, and a perimeter edge surface spanning between the interior surface and the exterior surface, the perimeter edge surface defining opposing planar portions oriented parallel to one another, a first end portion spanning between the planar portions, and a second end portion opposite the first end portion and spanning between the planar portions, each of the first end portion and the second end portion are curved,
   wherein the cover glass is an oblong shape, and
   wherein the cover glass extends, in a first plane, over a first angle range and, in a second plane which is perpendicular to the first plane, over a second angle range, wherein the first angle range is larger than the second angle range.

2. The endoscope according to claim 1, wherein the first angle range is at least 1.5 times as large as the second angle range.

3. The endoscope according to claim 1, wherein at least one of the interior surface and the exterior surface are antireflection-coated.

4. The endoscope according to claim 1, wherein the cover glass is formed as a sapphire cover glass.

5. The endoscope according to claim 1, wherein an edge of the cover glass is soldered to the distal end of the first tube.

6. The endoscope according to claim 1, wherein the imaging optics include a swivellably housed deflecting element with which a viewing direction through the cover glass can be set.

7. The endoscope according to claim 6, wherein a center of a radius of curvature of each of the interior surface and the exterior surface coincide and lie on a swivel axis of the deflecting element.

8. The endoscope according to claim 6, wherein the deflecting element includes a surface that brings about a beam deflection, a center of a radius of curvature of each of the interior surface and the exterior surface coincide and lie in the surface that brings about the beam deflection.

9. The endoscope according to claim 1, wherein the perimeter edge surface is inclined relative to a radius of curvature of the interior surface and the exterior surface.

10. The endoscope according to claim 1, wherein a vertex lines of the curved first and second end portions are tilted towards each other by 90°.

11. The endoscope according to claim 1, wherein the imaging optics include several lenses, wherein the lens of the imaging optics positioned closest to the cover glass is formed as a flat-concave lens a flat side of which faces the cover glass.

12. The endoscope according to claim 1, wherein the imaging optics include several lenses, wherein the lens of the imaging optics positioned closest to the cover glass is formed as a concave-concave lens.

13. An endoscope, comprising:
    a first tube; and
    a cover glass arranged at a distal end of the first tube, as well as with imaging optics;
       arranged in the first tube, which image an object located in front of the cover glass as an image,
    wherein the cover glass has a spherically curved, concave interior surface, a spherically curved, convex exterior surface, a constant thickness, and a perimeter edge surface spanning between the interior surface and the exterior surface, the perimeter edge surface defining opposing planar portions oriented parallel to one another, a first end portion spanning between the planar portions, and a second end portion opposite the first end portion and spanning between the planar portions, each of the first end portion and the second end portion are curved,
    wherein the cover glass is an oblong shape,
    wherein the cover glass extends, in a first plane, over a first angle range and, in a second plane which is perpendicular to the first plane, over a second angle range, wherein the first angle range is larger than the second angle range, and
    wherein a vertex lines of the curved first and second end portions are tilted towards each other by 90°.

14. The endoscope according to claim 13, wherein the perimeter edge surface is inclined relative to a radius of curvature of the interior surface and the exterior surface.

15. An endoscope, comprising:
    a first tube; and
    a cover glass arranged at a distal end of the first tube, as well as with imaging optics;
       arranged in the first tube, which image an object located in front of the cover glass as an image,
    wherein the cover glass has a spherically curved, concave interior surface, a spherically curved, convex exterior surface, a constant thickness, and a perimeter edge surface spanning between the interior surface and the exterior surface, the perimeter edge surface defining opposing planar portions extending along each of a first and a second major length of the cover glass that are oriented parallel to one another, a first end portion spanning between the planar portions, and a second end portion opposite the first end portion and spanning between the planar portions, each of the first end portion and the second end portion are curved,
    wherein the cover glass is an oblong shape,
    wherein the cover glass extends, in a first plane, over a first angle range and, in a second plane which is perpendicular to the first plane, over a second angle range, wherein the first angle range is larger than the second angle range.

16. The endoscope according to claim 15, wherein a vertex lines of the curved first and second end portions are tilted towards each other by 90°.

* * * * *